United States Patent
Kalkbrenner

(10) Patent No.: US 10,042,153 B2
(45) Date of Patent: Aug. 7, 2018

(54) MICROSCOPE AND METHOD FOR 3D HIGH-RESOLUTION LOCALIZATION MICROSCOPY WITH AN ENLARGED MEASUREMENT REGION

(71) Applicant: Carl Zeiss Microscopy GmbH, Jena (DE)

(72) Inventor: Thomas Kalkbrenner, Jena (DE)

(73) Assignee: Carl Zeiss Microscopy GmbH, Jena (DE)

( * ) Notice: Subject to any disclaimer, the term of this patent is extended or adjusted under 35 U.S.C. 154(b) by 137 days.

(21) Appl. No.: 14/889,417

(22) PCT Filed: Apr. 25, 2014

(86) PCT No.: PCT/EP2014/058451
§ 371 (c)(1),
(2) Date: Nov. 5, 2015

(87) PCT Pub. No.: WO2014/180680
PCT Pub. Date: Nov. 13, 2014

(65) Prior Publication Data
US 2016/0085062 A1    Mar. 24, 2016

(30) Foreign Application Priority Data

May 7, 2013  (DE) .......................... 10 2013 208 415

(51) Int. Cl.
| | |
|---|---|
| *G02B 21/36* | (2006.01) |
| *G02B 5/30* | (2006.01) |
| *G02B 21/00* | (2006.01) |
| *G02B 21/16* | (2006.01) |
| *G02B 21/18* | (2006.01) |

(Continued)

(52) U.S. Cl.
CPC ....... *G02B 21/367* (2013.01); *G01N 21/6458* (2013.01); *G02B 5/3083* (2013.01);
(Continued)

(58) Field of Classification Search
CPC .. G02B 21/367; G02B 5/3083; G02B 21/006; G02B 21/16; G02B 21/18; G02B 21/361;
(Continued)

(56) References Cited

FOREIGN PATENT DOCUMENTS

| | | |
|---|---|---|
| DE | 10 2006 021 317 B3 | 10/2007 |
| DE | 10 2009 060490 A1 | 6/2011 |

(Continued)

OTHER PUBLICATIONS

Rama et al., "Polarization Sensitive,Three-Dimensional, Single Molecule Imaging of Cells with a Double-Helix System," Optics Express, vol. 17, No. 22, Oct. 26, 2009 p. 19644-55.*

(Continued)

*Primary Examiner* — Thai Tran
*Assistant Examiner* — Christopher T Braniff
(74) *Attorney, Agent, or Firm* — Duane Morris LLP

(57) ABSTRACT

A microscope for high-resolution imaging of a sample in a depth direction and transversely thereto has an excitation beam path for illuminating a sample,—an imaging beam path with an objective and two detectors,—and a phase element. The phase element is situated in a pupil of the imaging beam path and has a different influence on two halves of the pupil cross section. The imaging beam path is split into two partial imaging beam paths downstream of the pupil as seen in the imaging direction, which partial imaging beam paths each lead to one of the two detectors. The two partial imaging beam paths have imaging lengths that differ by a specific wavelength difference such that the two detectors record images of the sample from two different focal planes, which are spaced apart by a distance in the depth direction.

5 Claims, 6 Drawing Sheets

(51) Int. Cl.
G01N 21/64 (2006.01)
H04N 13/20 (2018.01)
H04N 13/271 (2018.01)

(52) U.S. Cl.
CPC .......... *G02B 21/006* (2013.01); *G02B 21/16* (2013.01); *G02B 21/18* (2013.01); *G02B 21/361* (2013.01); *H04N 13/20* (2018.05); *H04N 13/271* (2018.05)

(58) Field of Classification Search
CPC . G01N 21/6458; H04N 13/02; H04N 13/0271
See application file for complete search history.

(56) References Cited

FOREIGN PATENT DOCUMENTS

| DE | 10 2010 044031 A1 | | 5/2012 |
|---|---|---|---|
| WO | WO 2006/127692 A2 | | 11/2006 |
| WO | WO 2011/085766 A1 | | 7/2011 |
| WO | WO2011085766 | * | 7/2011 |
| WO | WO 2012/039636 A2 | | 3/2012 |
| WO | WO2012039636 | * | 3/2012 |

OTHER PUBLICATIONS

Pavani, Sri Rama, et al.; "Polarization sensitive, three-dimensional, single-molecule imaging of cells with a double-helix system"; Optics Express 2009; 17(22) 19644-19655.

Huang, Bo, et al.; "Three Dimensional Super-Resolution Imaging by Stochastic Optical Reconstruction Microscopy"; Science 2008; 319:810-813 with Supporting Online Material.

Shtengel, Gleb, et al.; "Interferometric fluorescent super-resolution microscopy resolves 3D cellular ultrastructure"; PNAS 2009; 106(9):3125-3130.

Toprak, Erdal, et al.; "Three-Dimensional Particle Tracking via Bifocal Imaging" Nano Letters 2007; 7(7):2043-2045 with Supplemental Methods.

Juette, Manuel F., et al.; "Three-dimensional sub-100 nm resolution fluorescence microscopy of thick samples"; Nature Methods 2008; 5(6):527-529.

Keller,et al.;"Quantitative in Vivo Imaging of Entire Embryos with Digital Scanned Laser Light Sheet Fluorescence Microscopy";Current Opinion in Neurobiology 2008;18:624-632.

Pavani,et al.;"Three-dimensional, single-molecule fluorescence imaging beyond the diffraction limit by using a double-helix point spread function";PNAS 2009;106(9):2995-2999.

Notification of Transmittal of Translation of International Preliminary Report on Patentability, International Preliminary Report on Patentability, Written Opinion.

Baddeley, David, et al.; "Three-Dimensional Sub-100 nm Super-Resolution Imaging of Biological Samples Using a Phase Ramp in the Objective Pupil"; Nano Res. 2011; 4(6):589-598.

Huang, Bo, et al.; "Three-Dimensional Super-Resolution Imaging by Stochastic Optical Reconstruction Microscopy"; Science 2008; 319:810-813.

Toprak, Erdal, et al.; "Three-Dimensional Particle Tracking via Bifocal Imaging"; Nano Letters 2007; 7(7):2043-2045.

* cited by examiner

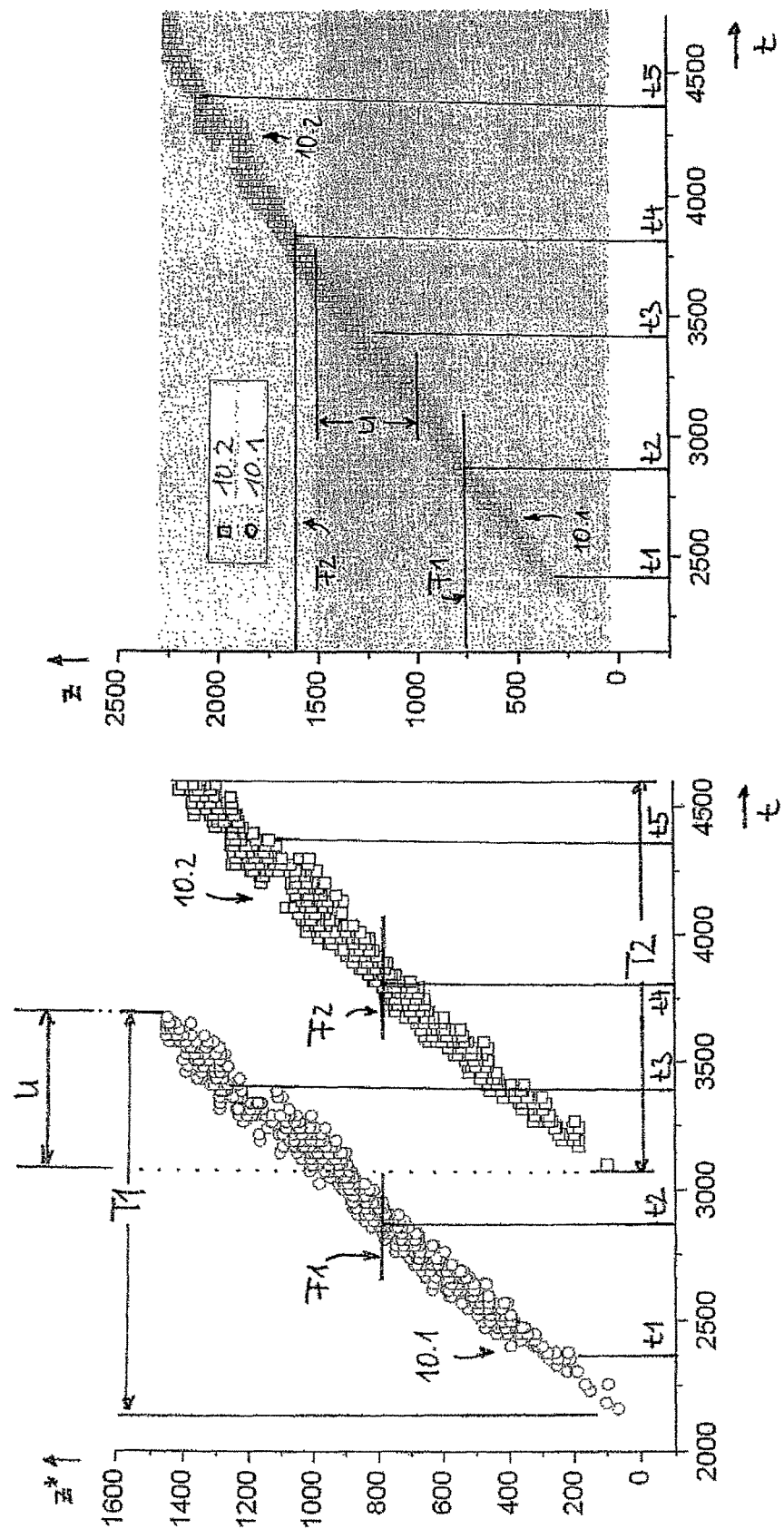

MICROSCOPE AND METHOD FOR 3D HIGH-RESOLUTION LOCALIZATION MICROSCOPY WITH AN ENLARGED MEASUREMENT REGION

RELATED APPLICATIONS

The present application is a U.S. National Stage application of International PCT Application No. PCT/EP2014/058451 filed on Apr. 25, 2014 which claims priority benefit of German Application No. DE 10 2013 208 415.3 filed on May 7, 2013, the contents of each are incorporated by reference in their entirety.

FIELD OF THE INVENTION

The invention pertains to a method of 3D high-resolution localization microscopy, wherein fluorescence emitters in a specimen are repeatedly excited to emit fluorescent radiation and individual images of the specimen are created with a microscope. The microscope has an imaging beam path with an optical resolution and a focal plane. The fluorescence emitters are excited to emit fluorescent radiation in such a way that at least one subset of the fluorescence emitters in each individual image is isolated so that the images of these fluorescence emitters can be separated within the optical resolution in the individual images.

BACKGROUND OF THE INVENTION

Various methods have been developed in the prior art for overcoming the diffraction limit in microscopy. From WO 2006/0127692 or DE 102006021317 A1 there is known a method, abbreviated as PALM (photo activated localization microscopy), which uses a marking substance for the imaging of a specimen, which can be activated by means of optical radiation. Only in the activated state can the marking substance emit a particular fluorescent radiation. Nonactivated molecules of the labeling substance, even after exposed to excitation radiation, emit no or substantially no noticeable fluorescent radiation with the defined properties. One therefore generally refers to the activation radiation as a switching signal. In the PALM method, the switching signal is supplied such that at least some of the activated marking molecules are so far away from neighboring activated marking molecules that they are separate in regard to the optical resolution of the microscope or can be separated afterwards by image processing methods. One speaks of fluorescence markers being isolated, and this step is also called an isolation step. It is enough to isolate a subset of the total group of fluorescence markers. The specimen is thus imaged; one obtains a single image of the specimen in which at least some of the fluorescence markers radiate in an isolated manner. Then, for each fluorescence marker, the center of the recorded radiation distribution is determined, which is not pointlike of course, due to the resolution limit. In this way, the position of the fluorescence marker is mathematically localized with higher precision than the optical resolution actually allows. This step is called the localization step.

The steps of isolation and localization are done repeatedly, so that one obtains several individual images. Ideally, each fluorescence marker is isolated once in at least one individual image. The position indications determined from the individual images make it possible to produce an overall image, containing the position indications of the individual fluorescence markers each time with an accuracy beyond the optical resolution. Such an image, having an accuracy beyond the optical resolution, is known as a high-resolution image.

The PALM principle utilizes statistical effects for isolating the fluorescence markers. In the case of a fluorescence marker which can be activated by the switching signal with a given intensity to emit fluorescence, one can ensure, by adjusting the intensity of the switching signal, that the probability of activating fluorescence markers present in a given surface region of the specimen, is so low that there are sufficient subregions in the imaged specimen in which at least some isolated fluorescence markers can be excited to emit fluorescent radiation within the optical resolution. The excitation of the so activated specimen then results in isolated radiating fluorescence markers.

PALM has been modified in regard to the activation, i.e., the supplying of the switching signal. Thus, for example, in the case of molecules having a long-lived nonfluorescing state and a short-lived fluorescing state, a separate activation with activation radiation different in spectrum from the excitation radiation is not even necessary. Instead, the specimen is at first illuminated with excitation radiation of high intensity so that the overwhelming majority of the molecules are brought into the nonfluorescent long-lived state (e.g., a triplet state). Then the remaining fluorescent molecules are isolated, at least in part.

The PALM principle has in the meantime also been referred to by other acronyms in the technical literature, such as STORM, etc. In this specification, we shall use the acronym PALM to identify all microscopy techniques which accomplish a high resolution by first isolating fluorescence markers and then localizing them. The PALM method has the advantage that no high spatial resolution is needed for the excitation. A simple wide-field illumination is possible.

The PALM principle achieves high resolution in 2D or laterally, i.e., transversely to the imaging direction, since the localization can only be done for fluorescence markers which are isolated in projection onto a plane lying perpendicular to the imaging direction. Fluorescence markers lying one behind another along the imaging direction, i.e., in the depth direction, cannot be distinguished with the PALM principle per se. The first experimental realizations of the PALM method therefore used a TIRF illumination, in order to make sure that fluorescence markers are only excited from a sharply defined depth region, which is substantially less than the depth of field of the imaging optics used.

Meanwhile, additional methods and approaches have been developed in the prior art which accomplish a 3D localization microscopy in which fluorescence markers are also isolated and localized in the third spatial dimension, i.e., the depth direction in regard to the imaging. By "depth direction" is meant the direction along the incident light, i.e., along the optical axis.

The publication of B. Huang et al., Science 319, page 810, 2008, describes an imaging beam path for the PALM principle in which a weak cylindrical lens is placed, causing a deliberate astigmatic distortion in the image. In this way, the image of each fluorescence marker is elliptically distorted on the camera whenever the fluorescence markers are located above or below the focal plane, representing a point of symmetry of the point spread function of the specimen imaging. From the orientation and the strength of the distortion one can gain information as to the depth position of the radiating fluorescence marker. One drawback of this method is that the local surroundings and orientation of a molecular dipole can also result in a distortion of the image of the radiating fluorescence marker, which has nothing to do with the depth position. Such radiating fluorescence markers then are given a false depth value, depending on their spatial position.

A different approach is taken by the publication of Shtengel et al., PNAS 106, page 3125, 2009. Here, photons emitted by the radiating fluorescence markers are caused to interfere with each other. For this, two objectives are used, mounted in a 4π configuration, which observe the radiating fluorescence markers at the same time. With the aid of a special 3-way beam splitter, the radiation from the so obtained partial beam paths is brought into interference. Each of the obtained images is detected with a camera, and the intensity relations of the images give an idea as to the depth position.

In the publication of Toprak et al., Nanolet. 7, pages 2043-2045, 2007, and also according to Juette et al., Nature Methods 5, page 527, 2008, a 1:1 beam splitter is installed in the imaging beam path, which splits up the image of the specimen into two subimages, which are detected independently. In addition, an optical path length difference is introduced in one of the partial beam paths after the beam splitter so that the two partial beam paths project two object planes which are separated by around half or the whole optical minimum resolution in the depth direction. The depth position of a fluorescence marker situated between these two object planes is found by analyzing the two partial images of this fluorescence marker (e.g., in terms of the width of the point spread). The method requires two highly resolved partial images and a subpixel-exact superpositioning of these two partial images. A modification of this approach which drastically reduces the adjustment expense is known from DE 102009060490 A1.

Another principle for gaining depth information for 3D localization microscopy is found in DE 102010044031 A1. This uses so-called light sheet illumination for the excitation and/or switching radiation, as described for example in the publication of P. Keller and E. Stelzer, "Quantitative In Vivo Imaging of Entire Embryos with Digital Scanned Laser Light Sheet Fluorescence Microscopy", Current Opinion in Neurobiology, 2008, Vol. 18, pages 624-632. The specimen is illuminated in succession by two axially offset, but overlapping light sheets. Molecules which emit fluorescent radiation in both positions of the light sheets must necessarily lie in the overlap region of the two light sheet positions. A suitable filtering is therefore done. In this way, the depth selection can be substantially boosted beyond the thickness of the light sheet. The thickness of the overlap region is critical to the filtering. The drawback to this approach is that twice the number of individual images have to be recorded for the localization, namely, for each light sheet position the number of single images that would be needed during traditional PALM imaging. The precise adjustment of the offset of the light sheets and especially the reproducibility of the adjustment is also important for the thickness of the overlap region and thus for the depth resolution. Finally, as a rule no meaningful resolution is possible any more within the filtered overlap region. Thus, the overlap region defines a kind of measurement uncertainty in regard to the depth indication. Fluorescence markers lying outside the overlap region cannot be specified in terms of their depth position, so that a detection of a region which is larger than the overlap region ultimately requires a scanning of the specimen.

In PAL microscopy, furthermore, an unwanted irradiation of the fluorescence markers can be a disadvantage, since the fluorescence markers often can only go through a very limited number of activation and/or excitation cycles. In this regard, any irradiation not utilized for a high-resolution imaging is undesirable.

One principle of depth resolution in localization microscopy employs a deliberate distortion of the point spread function (hereafter also abbreviated as PSF) of the imaging. Such an approach is described, for example, in WO 2012/039636, which modified the imaging of the specimen such that an image distortion is produced, which is dependent on the depth position. For example, the ideally spherical point spread function is modified so that for the imaging of a light spot we get two adjacent lobes instead of a diffraction disk, which are offset relative to each other depending on the depth position of the light spot being imaged.

The publication of Pavani et al., PNAS 106, page 2995, 2009, proposes modifying the point spread function by a 3D phase modulator in the imaging to produce a double helix structure. The point images of individual luminescent marking molecules than become double spots, and their depth position is coded in the angle orientation of the shared axis of the double spots.

What is common to the above mentioned 3D localization methods is the problem of a limited capture range, i.e., the range in which molecules can be detected and localized without intervention at the objective. Typically, this is at most 1 to 1.5 µm. This small capture range has the consequence that several slices or sections have to be recorded for a given z-dimension of the specimen being studied. This results in long recording time. Furthermore, generally while producing such slices areas of the specimen are excited which are not even used for the imaging. This represents an unwanted irradiation in the sense described above. Fluorescence emitters which undergo the activation and/or excitation cycles but were not used for the localization generally can no longer be used for another measurement, so that a complete imaging of the specimen may be difficult if not impossible.

SUMMARY OF THE INVENTION

The invention proposes to solve the problem of modifying the microscopy method of WO 2012/039636 so that a depth indication can be ascertained within a greater depth region. Furthermore, the invention solves the problem of indicating a depth-resolving microscopy method which prevents as much as possible the unwanted illumination of fluorescence markers.

The invention starts from the principle of depth resolution by deliberate distortion of the point spread function and broadens its capture range. The drawbacks in regard to unwanted illumination are thus avoided.

According to the invention, imaging of the specimen is done in several image planes situated one behind the other, corresponding to the different focal planes. This is accomplished by the imaging beam path being split into two partial imaging beam paths, which have different path lengths, after the pupil in which the manipulation of the PSF is performed. Thus, the two detectors of the partial imaging beam paths are coordinated with different focal planes. As compared to the concept of WO 2012/039636, this accomplishes an increased depth region or capture range, from which the depth position of the localized fluorescence emitters can be ascertained.

The phase manipulation occurs in a pupil of the imaging beam path, generally being a pupil conjugated with the pupil of the objective.

The spacing between the focal planes results from the path length difference of the partial beam paths. It is therefore preferable, when combining the pairs of individual images in terms of the depth indication in step e), to determine the distance between the focal planes on the basis of the path length differences of the partial beam paths.

The individual images are coordinated with different focal planes. In the x/y-direction, i.e., transversely to the depth direction, the individual images of each pair come from the same region of the specimen. In regard to a maximum covered depth region it would be advantageous to have the depth of focus regions which are characterized by a z region about the respective focal plane abut against each other as seamlessly as possible, yet also free of overlap. But it has been found that the joining of the individual images in step e) can be done with little expense if in step c) the distance by which the two different focal planes are separated is smaller than a depth region in terms of which the indication of the position of the fluorescing fluorescence emitters in the depth direction is determined from the spots. In this way, the individual images of each simultaneous image pair overlap in the depth direction in an overlap region. The evaluation of fluorescence emitters which are present in both individual images of the pair of individual images greatly facilitates the combining of the simultaneous individual image pairs in regard to the depth indication. A fluorescence emitter which, for example, appears at the upper margin in regard to the z-indication in the individual image associated with the lower focal plane then lies at the lower margin in the higher situated individual image coordinated with the higher focal plane. Since, because of the isolation, there are always fluorescence emitters which are isolated in both individual images in terms of the z-indication, with the help of the spots of such fluorescence emitters one can correctly transform position indications which are determined from both of the individual images in the z-direction so that the different depth levels from which the two individual images come are properly taken into account.

Step e) basically corresponds to a calibration of the z-coordinate, i.e., the depth indication of the fluorescence emitters. In an individual image pair the individual images differ in terms of the depth position. Each individual image of an individual image pair makes it possible to ascertain a depth indication. The depth indications of the individual images are not directly comparable. They must be calibrated in regard to the relative position of the focal planes of the individual images of an individual image pair. Therefore, in the following description, the uncalibrated depth indications in the individual images shall be identified by the coordinate $z^*$. The $z^*$ coordinates which are determined for the depth indications from the individual images of an individual image pair are calibrated in step e) so that the different focal planes are taken into account. In this way, one obtains calibrated coordinates, which shall be called hereafter the z-coordinate. In the coordinate system x, y, z the positions of the isolated fluorescence emitters in the individual images of an individual image pair are indicated so that the assembly can occur to produce the full image. In the coordinate system x, y, $z^*$, the assembly would only be possible in regard to the x, y-coordinate, since the uncalibrated coordinate $z^*$ in the individual images of an individual image pair would not allow a comparison among the individual images of a pair. It is therefore preferable to perform step b) after step f). In step e), the $z^*$ indication determined from an individual image is modified for isolated fluorescence emitters so that it is displaced by the distance between the focal planes. Of course, one can also displace the $z^*$ indications from the two individual images in opposite direction by half the focal distance. If one uses the information from the overlap region, as mentioned above, it is easiest to obtain the distance of the focal planes by the different relative $z^*$ coordinate for the very same fluorescence emitter which appears in both individual images. One then uses a correlation between structures in the overlap region of the individual image pairs.

The phase element in the pupil produces a modification of the point spread function so that the spots of individual emitters have a non-rotational symmetrical contour. For example, they may consist of individual lobes whose relative position depends on the depth position of a fluorescence emitter. The relative position for example can be a rotation or a displacement perpendicular to an axis along which the lobes are spaced apart. Basically, the methods known from WO 2012/039636 can be used to modify the PSF.

The path length difference of the partial imaging beam path adjusts the distance of the focal planes and thus ultimately an overlap region between the depth regions of the individual images of the individual image pair. It is therefore preferable to provide a path length adjustment device in at least one of the two partial imaging beam paths for adjusting the distance between the two different focal planes.

By the imaging of a fluorescence emitter is meant its generally diffraction-limited point image.

Of course, the above mentioned and afterwards yet to be explained features can be used not only in the indicated combinations, but also in other combinations or standing alone, without leaving the scope of the present invention. Insofar as features of the method are mentioned in this description, they are realized in the operation of the microscope by an appropriately configured control unit. Similarly, a disclosure of functional features of the control unit also counts as a description of corresponding method features, e.g., steps.

BRIEF DESCRIPTION OF THE DRAWINGS

The invention will be explained more closely hereafter with the help of the enclosed drawings, which also disclose features essential to the invention. The annexed drawings include the following:

FIGS. 5 and 6 are diagrams to illustrate an enlarged capture range of the microscope of FIG. 1.

DETAILED DESCRIPTION OF THE EMBODIMENTS

Figure 1:
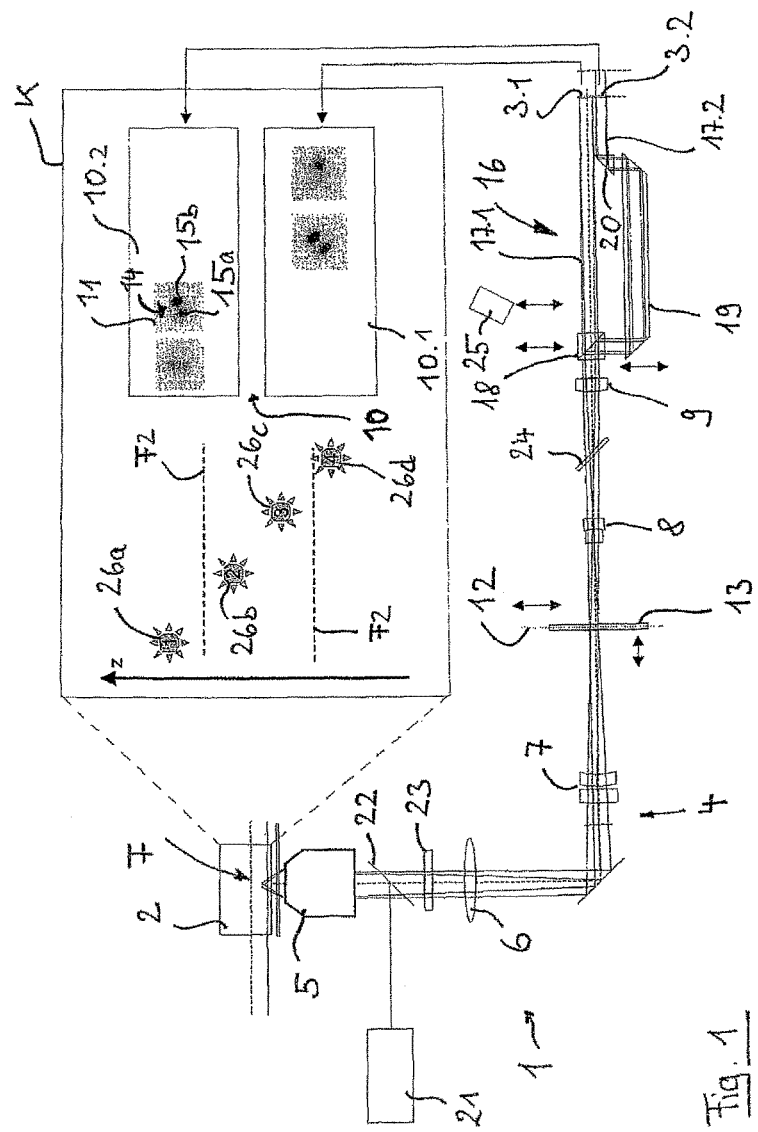
FIG. 1 is a diagram of a microscope for PAL microscopy.

FIG. 1 shows a microscope 1 designed to image a specimen 2 by means of the PALM principle. The specimen 2 is imaged on two detectors 3.1, 3.2 by an imaging beam path 4. The imaging beam path 4 has an objective 5 as well as a tube lens 6, which through additional optics 7, 8, 9 project a region of the specimen 2 situated in a focal plane F onto the detectors 3.1, 3.2. The imaging beam path 4, as will be further explained below, has a different optical path lengths for the two detectors 3.1 and 3.2, so that the two detectors 3.1 and 3.2 are associated with different focal planes F. This will be further explained below. As a result, the two detectors 3.1 and 3.2 provide an individual image pair 10 consisting of two individual images 10.1 and 10.2. These are represented schematically in the box K. With the imaging layout described thus far, one would expect that a radiating fluorescence emitter in the specimen 2 appears as a circular spot in the individual image 10.1 or 10.2, whose diameter depends on the depth position of the fluorescence emitter, i.e., it depends on exactly how far the fluorescence emitter lies in the focal plane associated with the detector 3.1 or 3.2 or how far away from that it is. In this way, however, PAL microscopy is unable to obtain any useful indication as to the depth position of the fluorescence emitter. For example, one would not know whether a fluorescence emitter lies above or below the focal plane.

In order to have an indication as to the position of a fluorescence emitter in the depth direction, i.e., in the direction perpendicular to the imaging direction of the objective 5, the imaging beam path 4 is altered such that the image 11 of a fluorescence emitter is no longer a circular spot.

Individual image 10.1 and 10.2 shows the images 11 of a fluorescence emitter for different depth positions. The images do not contain rotationally symmetrical spots on account of an intervention in a conjugated pupil plane 12 of the imaging beam path 4. The pupil plane 12 is provided by the optics 7, 8, 9. Arranged in it is an element for the pupil manipulation. This is a glass wedge 13 covering one half of the pupil, as is known from WO 2012/039636 for the generating of a helical PSF. The glass wedge 13 has the effect that each spot 14 of the image 11 of a fluorescence emitter is not rotationally symmetrical and it consists of two lobes 15a, 15b, whose relative position depends on the depth position of the fluorescence emitter. Individual image 10.1 for example contains the images 11 of two fluorescence emitters 26a and 26b, which lie in different attitude to the focal plane F1 associated with the corresponding detector 3.2. As can be seen from the images 11 of the fluorescence emitters 26a and 26b (the left image 11 in the individual image 10.2 is associated with the fluorescence emitter 26a, the right image 11 with the fluorescence emitter 26b), the relative position of the lobes changes with the depth position of the fluorescence emitter in regard to the focal plane F2 of the imaging on the detector 3.2. The same holds for the individual image 10.1, showing images of fluorescence emitters 26c, 26d.

The images shown alongside each other and isolated in the individual images 10.1 and 10.2 are ensured by the PALM principle, whose description in the aforementioned WO 2006/0127692 and DE 102006021317 A1 is incorporated here in its entirety, insofar as the required steps and measures for the isolating and localizing of fluorescence emitter are concerned.

The different focal planes F1 and F2 are produced by a divided section 16 of the imaging beam path 4. This has two partial beam paths 17.1, 17.2, which lead to the detectors 3.1, 3.2. The partial beam paths are divided by a beam splitter 18 in the imaging beam path 4. The partial beam path 17.2 experiences a threefold deflection by two prisms 19, 20, which displace the imaging beam path in parallel with the partial beam path 17.1 and lengthen it. The parallel offset means that the detectors 3.1 and 3.2 lie alongside each other, preferably being sections of a larger detector window of a single camera. The prism 19 can be moved in the direction of the schematically indicated arrow. In this way, the path length enlargement of the partial beam path 17.2 relative to the partial beam path 17.1 is adjusted. Thus, the shifting of the prism 19 is an example of a path length adjustment. Other measures are known to the skilled person for this, such as the use of adaptive mirror optics, DMD, or displacement of one of the two detectors.

The microscope 21 further has an illumination source 21, which couples illumination radiation across a beam splitter 21 into the imaging beam path 4, but opposite the imaging direction, and thus provides the activation radiation and excitation radiation needed for the PALM principle. A filter 23 filters out any back reflections of this radiation in the imaging beam path 4.

Another beam path 24 in the imaging beam path 4 makes it possible to couple out an image onto a tube sight or a second color channel.

In the case when only a single individual image 10 is to be used, the beam splitter 18 can be swiveled out from the beam path. In this way, the separation of the partial beam path 17.2 does not occur, and one gets only the individual image 10.1. A plane parallel plate 25 then makes it possible, when the beam splitter 18 is swiveled out, to place the image on the center of the camera, which provides the detectors 3.1 and 3.2 through different sections of its image window. By appropriate adjustment of the optics 7, 8, 9 the image can then be enlarged on the camera, so that the de facto two detectors 3.1 and 3.2 are used to generate a single image. This operating mode has a small capture range.

In the representation of FIG. 1 the condition is shown in the operating mode with larger capture range (beam splitter 18 engaged, plate 25 disengaged). Now the focal plane F coincides with the focal plane F1. This is shown by the broken line plane, in which the detectors 3.1 and 3.2 lie. The focal plane F2, however, on account of the lengthening effect of the partial beam path 17.1, is shifted into the specimen relative to the focal plane F. This configuration has the advantage that the partial beam path 17.2 can be easily deactivated, namely, by swiveling out of the beam splitter 18.

The radiating fluorescence emitters 26a-d in the individual images 10.1 and 10.2 are localized in three dimensions by adapting a suitable experimental or simulated PSF, as is known from the mentioned WO 2012/039636, which is incorporated in the full extent of its disclosure for this purpose. Thus, for each individual image 10.1, 10.2 we get a high-resolution 3D data set with coordinates x, y, z*, which covers that depth region lying around the respective focal plane F1, F2. Since the focal plane distance is known on account of the path length difference of the partial beam paths 17.1, 17.2, the simultaneously obtained 3D data sets can be combined by calibration of the z*-coordinate into an overall image with coordinates x, y, z, encompassing a greater depth region. This will be explained below with the aid of FIGS. 5 and 6.

Figure 2:
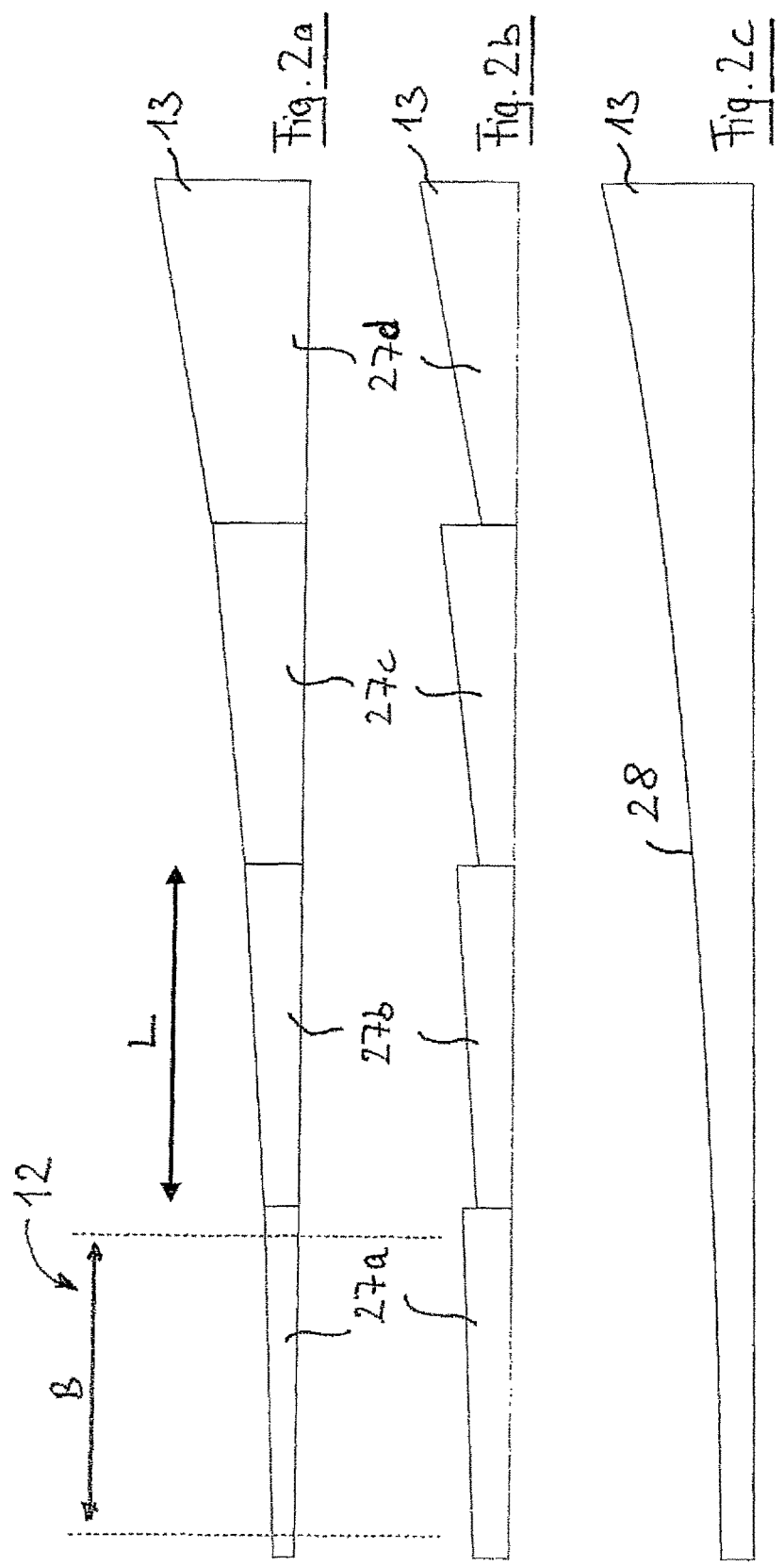
FIG. 2 is schematic sectional views of glass wedges, which are arranged on one pupil half of an imaging beam path of the microscope of FIG. 1 and produce a phase shifting to generate a PSF modification.

FIG. 2a-c show possible configurations for the pupil-manipulating element, with which an adjustment of the pupil manipulation is possible. The figures show three glass wedges 13, consisting for example of four segments, each having a length L. The length L is smaller than a width B of the imaging beam path 4 in the pupil plane 12. The four segments 27a-d differ in their PSF-modifying effect, which is defined by the wedge angle. In other words, the four segments 27a-d have a different wedge angle. By displacement of the glass wedge 13 in the pupil plane 12 transversely to the direction of the principal axis of the imaging beam path 4, one can switch between the individual segments 27a-d and thus adjust a different wedge angle.

The glass wedge 13 of FIG. 2b basically corresponds to that of FIG. 2a. However, the mean glass thickness is the same for all segments 27a-d here, which is advantageous from the standpoint of the glass paths.

Figure 3:
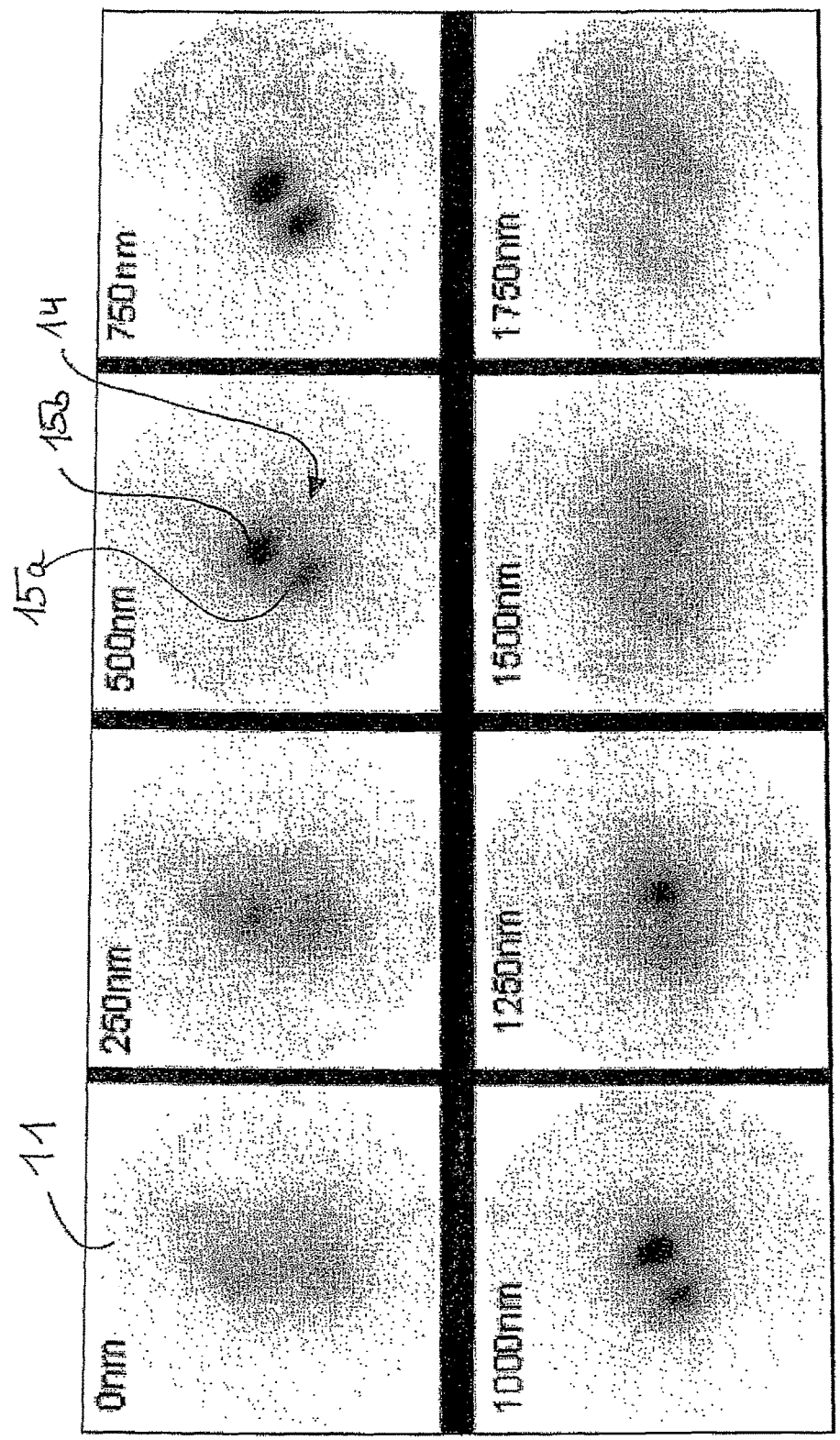
FIGS. 3 and 4 are diagrams of image changes which are produced by the PSF modification.

FIG. 2c shows a glass wedge with a continuously increasing gradient 28. Accordingly, it can be displaced continuously transverse to the optical axis of the imaging beam path 4 and it allows a continuous adjustment of the PSF modification, while the glass wedges 13 of FIG. 2a, 2b can only be adjusted by increments, so that the width B always lies entirely in one of the segments 27a-d FIG. 3 shows as an example the effect of the phase intervention in the pupil 13. One sees images 11 of a fluorescence emitter whose depth position is different. The images were taken by moving a point emitter upward in steps of 1.75μ from a lowermost plane lying beneath a focal plane F1 or F2. The lowermost plane here was 875 nm beneath the focal plane. As can be seen, the spot 14 changes in regard to the relative position of its lobes 15a, 15b depending on the depth. In the lowermost plane, indicated as 0 nm, there is a relative position which rotates counterclockwise with increasing levels (in the image of FIG. 3 a step width of 250 nm was chosen). Thus, from the relative position of the lobes the depth position of the fluorescence emitter can be reliably deduced.

Figure 4:
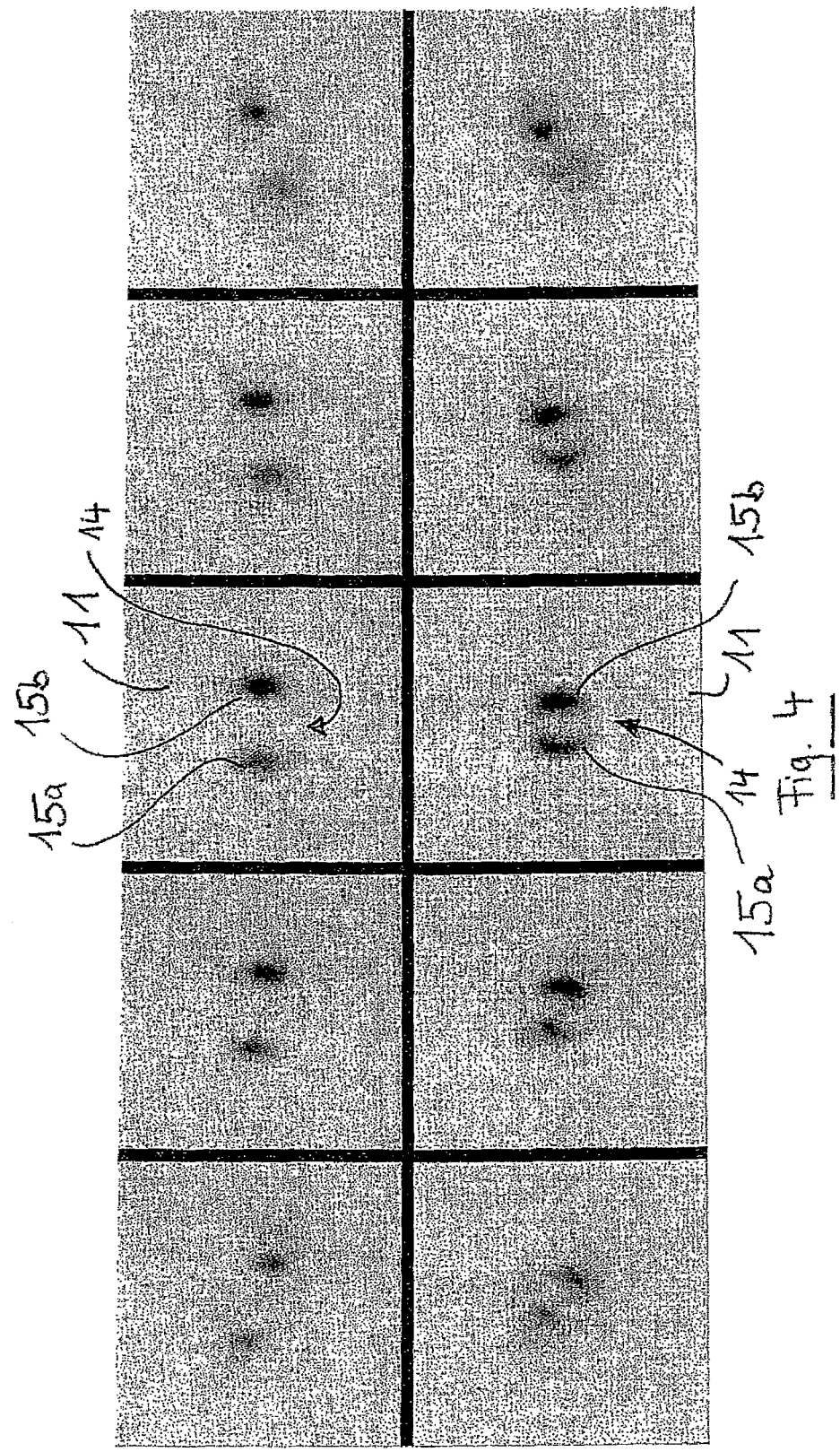

FIG. 4 shows a configuration which has an opposite offset, differing in regard to intensity, of the lobes 15a, 15b along an axis which lies transversely to the axis along which the lobes 15a, 15b are spaced apart. The two lines of FIG. 4 differ in the angle of inclination of the glass wedge, i.e., the intensity of the phase ramp representing the glass wedge 13. The middle image of each series is obtained from a fluorescence emitter situated exactly in the focal plane. From the representation of FIG. 4 (as also that of FIG. 3) it is easy to notice that the relative position of the lobes 15a, 15b reflects not only the magnitude, but also the direction of the distance from the focal plane.

FIG. 5 schematically shows measurements on a fluorescing emitter with the microscope of FIG. 1. One and the same fluorescence emitter was moved here in a linear manner across the capture range of the two images. On the abscissa is plotted the time. The depth coordinate in FIG. 5 is designated as $z^*$, since the indications and plots in the representation of FIG. 5 for the two individual images do not yet take into account the different position of the focal planes F1 and F2. In the $z^*$ coordinates the focal planes F1 and F2 lie in the same place. Also, each individual image captures the same depth region in $z^*$ coordinates. In order to illustrate the difference of the depth regions and the overlap region U, T1 and T2 have been plotted along the time coordinate t. This is permissible in FIG. 5, because here a fluorescence emitter was moved uniformly, i.e., continuously in time across the entire capture range of the microscope, resulting from the dimension T1+T2−U.

One clearly identifies the overlap from the fact that the fluorescence emitter at first appears only in image 10.1 and then, when the overlap region U begins, it also turns up in the second individual image 10.2. It is present in both individual images for as long as T1 and T2 overlap. Only outside of the overlap region U is the image of the fluorescence emitter present only still in the second individual image 10.2.

The position indications which were extracted from the individual image 10.1 are designated by circular points, the position indications from the individual image 10.2 with small squares. The width of the depth regions T1, T2 is dictated by the optics of the imaging beam path 4. For the individual images 10.1 and 10.2, different depth regions T1, T2 result, yet being identical in size. The particular focal plane F1, F2 is the center of the corresponding depth region T1, T2.

If one considers, for example, the time t1, the fluorescence emitter appears only in the individual image 10.1, since it lies in the depth region T1, but not T2. At t2 the fluorescence emitter is projected exactly in focus in the individual image 10.1, since it is situated in the focal plane F1. The spot here also is not circular of course, on account of the already described modification of the point spread function.

At time t3 the fluorescence emitter appears in both individual images, but it has there different relative $z^*$ coordinates. In the individual image 10.1 the fluorescence emitter is detected with a high relative $z^*$ coordinate, in the individual image 10.2 with a low one. At t4, finally, the fluorescence emitter is projected directly from the focal plane F2 and likewise appears exclusively in the individual image 10.2, as at coordinate t5.

The overlap region U is known. This makes it possible to convert the relative $z^*$ coordinates into absolute z-coordinates. For this, in a first embodiment, the distance between focal planes F1 and F2 is evaluated. For example, each $z^*$ coordinate from the individual image 10.2 is shifted upward by the focal spacing |F2−F1|. Alternatively, an analogous opposite shifting (i.e., downward) of the $z^*$ coordinate values in the individual image 10.2 can be done.

In a second embodiment, the overlap region U between the depth regions T1 and T2 is determined and by suitable calibration of the $z^*$ coordinates it is balanced out. In a third embodiment, fluorescence emitters lying in the overlap region U are localized in regard to their $z^*$ coordinates in the individual images 10.1 and 10.2. The difference of the $z^*$ coordinates from the two individual images then indicates the necessary displacement for the calibration. It is possible here to evaluate several fluorescence emitters lying in the overlap region U and thus statistically improve the offset needed for the calibration, i.e., the displacement of the $z^*$ coordinates to obtain the z-coordinate.

FIG. 6 shows the situation obtained after the calibration, in which the individual images 10.1 and 10.2 indicate the fluorescence emitters, in turn represented by circular and square points, also positionally correct in regard to the z-coordinates. The individual images are put together to form the total image. In the representation of FIG. 6 the focal planes F1 and F2 are not spaced apart on account of the plotting in z-coordinates and no longer at the same depth coordinate, as in the representation of FIG. 5, which used $z^*$ coordinates. Also, in FIG. 6 the overlap region U is now plotted for better clarity in the z-direction. It is clearly recognized as the region in which the image of the fluorescence emitter was recorded both in the individual image 10.1 (thus plotted with circle symbols) and in the individual image 10.2 (therefore plotted with squares).

The different representation of the overlap region U in FIGS. 5 and 6 is used only for easier visibility. In actuality, as already mentioned, the depth regions T1 and T2 as well as the overlap region U are given in the depth direction, i.e., in the direction of the z-coordinate. For the representation in FIG. 5 in relative $z^*$ coordinates, however, the focal planes F1 and F2 and thus also the depth region T1 and T2 coincide on the ordinate, so that they have been plotted in FIG. 5 along the abscissa for better clarity. Since the fluorescence emitter has been displaced uniformly in time in the depth direction in order to obtain the coordinates on which the images of FIG. 5 and FIG. 6 are based, the simplification done in FIG. 5 is permissible.

Figure 7:
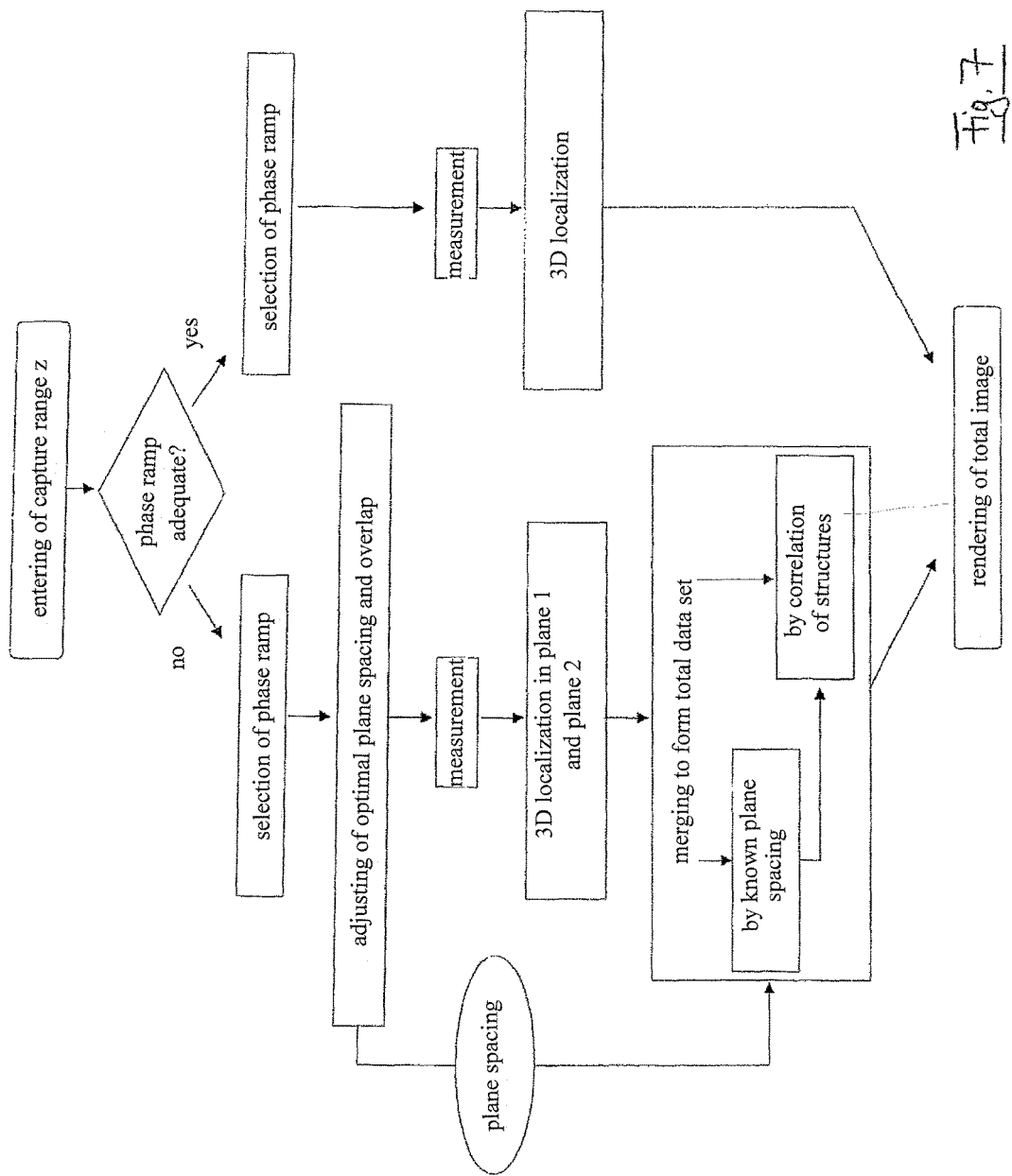
FIG. 7 is a flow chart for a possible microscopy method with the microscope of FIG. 1.

The microscope or microscopy method according to the invention makes it possible to adjust the capture range of the depth resolution. A flow chart is shown in FIG. 7. After setting a capture range, for example, after entering the capture range into a computing device (not shown in FIG. 1), it is determined whether a phase ramp alone is sufficient for this capture range. The limitation of the phase ramp, as can be easily seen from FIG. 3, results from the fact that the individual lobes 15a, 15b of the spot 14 become increasingly blurred under extreme deviations of the focal plane. If the use of the phase ramp by itself is sufficient, the suitable phase ramp will be chosen. At the same time, the beam splitter 18 is swiveled out and the plate 25 swiveled in, so as to obtain the full image region from the merging of detector 3.1 and 3.2. In the following PAL microscopy, the 3D localization measurement is done as usual. This is one option of the method. It is not necessary to use it.

If one wishes a larger capture range for which the phase ramp alone is not enough, the suitable phase ramp is selected, the phase ramp being chosen so that it covers at least 50% of the desired capture range. From this possible capture range with the aid of the phase ramp, the corresponding spacing of the focal planes F1, F2 and the overlap U is adjusted. After measurement and localization in the individual images 10.1 and 10.2, these are combined into a total data set, it being possible to do this with regard to the z-coordinate (as described above) thanks to the already known spacing between the focal planes F1 and F2 or by correlation of fluorescence emitters which appear in both individual images 10.1 and 10.2. As a result, one obtains a total image with a larger capture range.

In regard to the microscope, various modifications of the described embodiments are possible in the framework of the invention. The following options shall be mentioned as examples:

The microscopy method or the microscope manipulate the PSF of the imaging. In the embodiments, a dispersive element in the form of a glass wedge is installed in one half of the imaging pupil. The PSF manipulation need not necessarily be done in one pupil. A certain spacing of the pupil is also possible, for example, if the pupil is not entirely accessible in the imaging beam path. Moreover, the manipulative intervention is not limited to influencing half of a beam path. It is also possible to undertake an intervention in the entire cross section of the beam path, if this is done in opposite direction. An example of such an opposite intervention is found in the cited WO 2012/039636 in the form of glass wedges which run in opposite direction in two halves of the beam cross section. The measures mentioned in the WO document can of course be used equally for the PSF modification. Neither is a PSF modification limited to the use of transmissive elements. Reflective elements, such as suitable mirror elements and especially adjustable reflective elements like DMD can equally be used for the modification of the PSF in the context of the invention.

The microscope according to the invention advantageously uses adjacent segments of a camera to realize the two detectors. These then lie necessarily in the same plane, and a beam path leading to one of the detectors is longer than the other one leading to the other detector. Of course, separate detectors can also be used, lying in different optical path length to the imaging optics. Thus, for example, the beam splitter 18 can be used to separate the beam paths, without having to bring together the beam paths once again in parallel situated sections. The detector 3.2 in the representation of FIG. 1 would then lie near the lower image margin, rotated by 90°.

In the embodiments, an adjusting of the beam path to one of the detectors is described for the adjusting of the relative position of the focal planes F1 and F2. Of course, one can also leave the beam path alone and shift one of the detectors, if independent detector elements are being used.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed is:

1. A method for 3D high-resolution localization microscopy, for imaging a specimen with high resolution in a depth direction and transversely thereto, comprising
   a) exciting fluorescence emitters in the specimen to emit fluorescent radiation, generating with a microscope individual images of the specimen, said microscope having an imaging beam path with an optical resolution, said fluorescence emitters being excited to emit fluorescent radiation such that at least some of the fluorescing fluorescence emitters in each individual image are isolated so that the images of said fluorescing fluorescence emitters can be separated within the optical resolution in the individual images,
   b) forming a spot with a non-rotation symmetrical contour as an image of each of the fluorescing fluorescence emitters by means of a phase element which is placed in a pupil of the imaging beam path and which differently influences two halves of the pupil cross section, wherein a relative position of components of each spot depends on the position of the particular fluorescing fluorescence emitter in the depth direction,
   c) splitting the imaging beam path into two partial imaging beam paths downstream from the pupil, in the imaging direction, each of them leading to one of two detectors, wherein the two partial imaging beam paths have imaging lengths differing by a particular path length difference, so that the two detectors record the individual image in the form of simultaneous individual image pairs of the same fluorescence state of the specimen from two different focal planes, a depth region surrounding each focal plane, said focal planes being separated by a distance in the depth direction, said depth regions seamlessly abutting against each other along the depth direction,
   d) deriving a depth indication for the position of the fluorescing fluorescence emitters in the depth direction from the relative positions of the components of the spots in each simultaneous individual image pair,
   e) evaluating positions of fluorescence emitters which are present in each image pairs for assembling the simultaneous individual image pairs in terms of the depth indication corresponding to the spacing of the focal planes or depth regions, and
   f) wherein in the simultaneous individual image pairs, before or after step e), for the fluorescing fluorescence emitters which can be separated within the optical resolution one localizes their positions in the depth direction and transversely to it with a positional accuracy beyond the optical resolution and from this generates a high-resolution total image of the thickness.

2. The method according to claim 1, further comprising determining the distance between the focal planes on the basis of the path length difference of the partial beam paths in step e).

3. A microscope for high-resolution imaging of a specimen in a depth direction and transversely thereto, comprising:
an excitation beam path for illuminating a specimen,
an imaging beam path with an objective and two detectors,
a phase element, standing in a pupil of the imaging beam path and influencing two halves of the pupil cross section in different ways, wherein
the imaging beam path is split into two partial imaging beam paths after the pupil, looking in the imaging direction, each of them leading to one of the two detectors, while the two partial imaging beam paths have imaging lengths differing by a particular path length difference, so that the two detectors record images of the specimen from two different focal planes, a depth region surrounding each focal plane, said focal planes being separated in the depth direction by a spacing, said depth regions seamlessly abutting against each other along the depth direction.

4. A microscope according to claim 3, wherein the phase element is configured as a glass wedge or ramp and it can be displaced in the pupil transversely to the optical axis in order to adjust the phase shifting effect.

5. A microscope according to claim 3, further comprising a path length adjustment device in one of the two partial imaging beam paths to adjust the spacing between the two different focal planes.

* * * * *